United States Patent
Kabbani et al.

(10) Patent No.: US 8,807,995 B2
(45) Date of Patent: Aug. 19, 2014

(54) TOOTH TOP PART

(75) Inventors: Robert Kabbani, Abu Dhabi (AE);
Juergen Bathen, McMinnville, OR (US); Rolf Hagelganz, Dundee, OR (US)

(73) Assignee: World Class Technology Corporation, McMinnville, OR (US)

( * ) Notice: Subject to any disclaimer, the term of this patent is extended or adjusted under 35 U.S.C. 154(b) by 0 days.

(21) Appl. No.: 13/568,594

(22) Filed: Aug. 7, 2012

(65) Prior Publication Data

US 2012/0301838 A1     Nov. 29, 2012

Related U.S. Application Data

(63) Continuation-in-part of application No. PCT/US2011/024067, filed on Feb. 8, 2011.

(30) Foreign Application Priority Data

Feb. 20, 2010  (DE) .......................... 10 2010 008 749

(51) Int. Cl.
*A61C 7/14*     (2006.01)
*A61C 7/30*     (2006.01)
*A61C 7/12*     (2006.01)

(52) U.S. Cl.
CPC ... *A61C 7/30* (2013.01); *A61C 7/12* (2013.01); *A61C 7/141* (2013.01); *A61C 7/14* (2013.01); *A61C 7/303* (2013.01)
USPC .......................................................... 433/8

(58) Field of Classification Search
USPC ........................... 433/8–24; 29/896.1, 896.11
See application file for complete search history.

(56) References Cited

U.S. PATENT DOCUMENTS

| | | | |
|---|---|---|---|
| 2,558,475 A | | 6/1951 | Broussard |
| 3,043,007 A | * | 7/1962 | Wallshein ......................... 433/8 |
| 3,052,028 A | * | 9/1962 | Wallshein ....................... 433/11 |
| 3,218,712 A | * | 11/1965 | Wallshein ....................... 433/16 |
| 3,327,393 A | * | 6/1967 | Brader ............................ 433/11 |
| 3,530,583 A | * | 9/1970 | Anderson et al. ............... 433/11 |
| 3,724,074 A | * | 4/1973 | Wallshein ....................... 433/11 |
| 4,846,681 A | * | 7/1989 | Mourany et al. ................ 433/11 |
| 6,485,299 B1 | | 11/2002 | Wildman |
| 7,033,170 B2 | | 4/2006 | Cordato |
| 2007/0082315 A1 | | 4/2007 | Sabater |

FOREIGN PATENT DOCUMENTS

| | | |
|---|---|---|
| DE | 20009331 U1 | 12/2000 |
| DE | 102004016317 B4 | 9/2007 |
| DE | 102007008356 B3 | 7/2008 |
| JP | 3146052 A | 6/1991 |

\* cited by examiner

*Primary Examiner* — Yogesh Patel
(74) *Attorney, Agent, or Firm* — Chernoff, Vilhauer, McClung & Stenzel LLP (57) ABSTRACT

The invention relates to a tooth top part for a tooth correction means (1), with a base body (2) at which a tooth support surface (5, 25, 45) is formed for being fixed at a tooth surface (3) by bonding, and which is provided with a guide recess (12, 32, 52) which is formed for receiving a connecting means (4, 24, 44) for coupling neighboring tooth top parts (2, 22, 42) and which passes through the base body (2) in spaced relationship to the tooth support surface (5) along a guiding axis (17). According to the invention, the base body (2) comprises a substantially triangular or circular section shaped cross section (11, 11a, 31, 51) in a cross sectional plane (10) normal to the guiding axis (17).

5 Claims, 6 Drawing Sheets

Prior Art

TOOTH TOP PART

CROSS-REFERENCE TO RELATED APPLICATIONS

This application is a continuation-in-part of pending application PCT/US2011/024067 filed Feb. 8, 2011, and is related to and claims priority from pending German application DE 10 2010 008 749 filed Feb. 20, 2010.

BACKGROUND OF THE INVENTION

1. Field of the Invention

This invention relates to orthodontic appliances and in particular to orthodontic brackets having a low profile between the top of the tooth and the inner lips so as to minimize irritation.

2. Description of Related Art Including Information Disclosed Under 37 CFR 1.97 and 1.98

Typically, orthodontic brackets have profiles that cause irritation of the inner lip surfaces of a patient because the bracket is rectangular in cross section and its edges protrude too far above the top of the tooth. Typical orthodontic bracket designs are shown in various U.S. patents such as Wildman et al. (U.S. Pat. No. 5,613,850), Damon (U.S. Pat. No. 5,466,151) and in published application no. US2004/0072117 to Farzin-Nia et al.

BRIEF SUMMARY OF THE INVENTION

An orthodontic appliance is applied to the top surface of a tooth and includes a base portion and an upper portion, the upper portion having a recess to receive an archwire, the base portion having a cross sectional shape in the form of a semi-circle or shallow triangle so as to minimize irritation of the inner lip of a patient.

The foregoing and other objectives, features, and advantages of the invention will be more readily understood upon consideration of the following detailed description of the invention, taken in conjunction with the accompanying drawings.

DETAILED DESCRIPTION OF PREFERRED EMBODIMENT

The invention relates to a tooth top part for a tooth correction means, with a base body at which a tooth support surface is formed for being fixed at a tooth surface by bonding, and which is provided with a guide recess which is formed for receiving a connecting means for coupling neighbouring tooth top parts and which passes through the base body in spaced relationship to the tooth support surface along a guiding axis.

A tooth top part of this type which is also referred to as a bracket, is known from DE 20 2009 008571 U1. The known tooth top part is formed at an outward-facing surface of a tooth for being fixed by bonding, and to that end comprises a tooth support surface which is used as an adhesive surface for adhesively attaching (adhering) the tooth top part to the surface of the tooth. The tooth top part is provided with a groove-type recess extending along a guiding axis and being spaced from the tooth support surface. The known tooth top part comprises a substantially H-shaped cross section in a cross sectional plane normal to the guiding axis. The recess in the tooth top part permits insertion of a connecting means, which couples tooth top parts attached to neighbouring teeth and permits transmission of forces between the teeth. The forces and, if applicable, the torques transmitted by the connecting means enable the teeth to move relative to each other and permit correction of false positioning (malocclusion) of teeth.

The tooth top part known from the prior art has a drawback that the H-shaped cross section, which may be approximated by a rectangular envelope (curve) in the cross sectional plane, causes irritations of the mouth mucous membrane (oral mucosa) in particular at the inside of the lips. This results in reduced wearing comfort for a tooth correction means formed by a plurality of such tooth top parts.

It is an object of the invention to provide a tooth top part which comprises improved adjustment to the anatomical conditions in the mouth region and thus causes less irritation of the mucous membranes.

This object is achieved in a tooth top part as mentioned in the above introduction using the features of claim 1 which provides that the base body comprises a substantially triangular or circular section shaped cross section in a cross sectional plane normal to the guiding axis.

The triangular or circular section shaped cross section guarantees reduced friction during relative movements between the tooth top parts and the opposing mucous membrane. Thus, due to the reduced friction, the mucous membranes will be irritated less both during talking and food intake, and discomfort caused by sore spots in the mucous membrane is reduced. Preferably, compared to known tooth top parts, these tooth top parts have a reduced overall height, which may provide a further reduction in mucous membrane irritations. Preferably, the height of the tooth top part in a direction normal to the tooth surface is less than 2.5 times, in particular less than 2 times, the largest edge length (for instance with a rectangular cross section) or the diameter of the connecting means. More preferably, the connecting means comprises a largest edge length or a diameter selected to be less than 0.5 mm, in particular less than 0.4 mm.

Further advantageous embodiments are presented in the sub-claims.

Appropriately, a base line of the substantially triangular or circular section shaped cross section is formed by the tooth support surface, and a mean perpendicular to the base line comprises a length less than 50 percent of the length of the base line. With this shape of the profile of the tooth top parts, an advantageous ratio is achieved between the size of the tooth support surface required for secure immobilization of the tooth top parts at the tooth surfaces and the height of the respective tooth top part. The length of the mean perpendicular corresponding to the maximum height of the tooth top part beyond the tooth surface is small compared to known tooth top parts. As a result, when combined with the triangular or circular section shaped cross section of the tooth top part, a particularly gentle use of the tooth correction means constituted with the tooth top parts according to the invention can be achieved.

Preferably, each of the outer surfaces of the base body, adjacent to the tooth support surface, include acute angles, preferably less than 45 degrees, more preferably less than 35 degrees, particularly less than 25 degrees, with the tooth support surface. The outer surfaces of the tooth top part are those surfaces at the base body that are in particularly intensive contact with the opposing mucous membranes of the mouth region. The smaller the selected angle between the outer surface and the tooth support surface, the greater the wearing comfort of the tooth correction means constituted by the tooth top parts. However, since reception of the connecting means is always required, the angles cannot be reduced at will.

The triangular cross section of the base body may be formed as an isosceles triangle having identical acute angles between the two outer surfaces and the tooth support surface. Alternatively, the triangular cross section may be formed as a triangle at will where the acute angles included between the respective outer surface and the tooth support surface are selected differently. The circular section shaped cross section may be selected as a symmetrical or asymmetrical circular section.

In a further improvement of the invention, transitional regions between the outer surfaces and/or between an outer surface and the tooth support surface are formed with a rounding-off radius. This avoids sharp edges at the transitions between the outer surfaces or between the outer surface and the tooth support surface which too could give rise to unwanted mucous membrane irritations.

Appropriately, the, preferably undercut, guide recess is formed as a groove-type indentation starting from one of the outer surfaces of the base body. A groove-type indentation enables comfortable and rapid insertion and, if required, removal of the preferably wire-shaped connecting means into the guide recess and from the guide recess, respectively. This is particularly true if the groove opening of the guide recess extends alongside the guiding axis of the guide recess, thus enabling insertion/removal of the connecting means crosswise/transverse to the direction of its overall extension. Preferably, the guide recess is formed with an undercut that, for instance, allows the connecting means to be locked within the guide recess.

Advantageously, at least one, preferably sectionally elastic, snap-on nose is formed at the base body, said snap-on nose regionally limiting the groove-type indentation and being formed for lockingly receiving the connecting means in the guide recess. The snap-on nose is meant to immobilize the connecting means at the tooth top part such that, on one hand, the latter is able to transmit the desired forces between adjacent teeth and, on the other hand, can be easily attached at the tooth top part and, if required, removed again therefrom.

Preferably, the snap-on nose is formed as an at least sectionally elastic spring nose enabling snap-in of the connecting means and self-locking, in particular positive locking (form-locking), immobilization of the connecting means at the tooth top part. Alternatively, the groove-type recess may also be closed using a separate locking element or a locking element integrally attached to the base body, wherein the locking element may, for instance, be shifted or swung/pivoted between a locked position and an open position.

In an advantageous improvement of the invention, the snap-on nose is formed for self-locking, in particular positive locking (form-locking), immobilization of the connecting means at the base body. With a self-locking design of the snap-on nose, the connecting means is pushed into the tooth top part while being elastically deformed and, when reaching a predetermined functional position, will be immobilized solely by the resilience (elastic restoration properties) of the snap-on nose without any effort by the user. Preferably, the connecting means, the guide recess in the tooth top part and the snap-on nose are coordinated such that immobilization of the connecting means by positive locking is achieved.

Preferably, the base body is made of a preferably tooth-colored, clear or translucent synthetic material (plastics material). This enables the tooth top parts to be inconspicuously arranged within the mouth region of a patient. More preferably, the tooth top parts are formed in different colorings and/or degrees of transparency in order to allow for low contrast adaptation to the respective tooth color.

Appropriately, the groove-type indentation is formed for lockingly receiving a profiled connecting means which is formed for transmitting torsional forces between neighbouring tooth top parts. This enhances the versatility of the tooth correction means made of the tooth top parts according to the invention by the possibility of inducing pivoting movements between neighbouring teeth. More preferably, the connecting means comprises a square or rectangular cross section which is at least partially mapped in the recess of the tooth top part in order to allow the transmission of torque between the connecting means and the tooth top part.

In an advantageous improvement of the invention, the groove-type indentation is adapted to the connecting means such that a, preferably low friction or nearly zero friction, relative movement of the connecting means with respect to the base body, in particular along/alongside the guiding axis of the recess is enabled. This allows particularly rapid correction of false positioning of teeth without requiring frequent readjustment of the connecting means. The mentioned coordination between the recess and the connecting means is also referred to as self-ligating, since the connecting means is free to move in the recesses of the tooth top parts in accordance with the patient's needs without requiring any additional elements such as rubber rings for immobilizing the connecting means at the tooth top parts.

Preferred embodiments of the invention are shown in the drawings.

Figure 1:
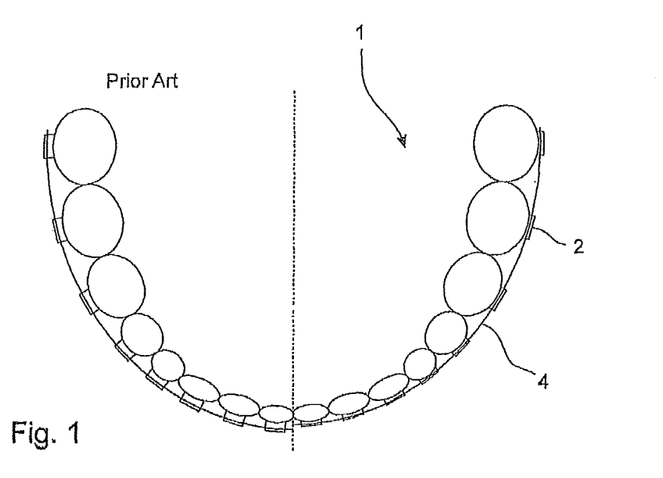
FIG. 1 is a schematic view of a tooth correction means formed of a plurality of tooth top parts and a connecting means.

In a human tooth arrangement schematically shown in FIG. 1 and comprising molars, canines and incisors, a tooth correction means 1 according to the prior art is shown in the left-hand region of FIG. 1, whereas a tooth correction means according to the invention is shown in the right-hand region of FIG. 1. Both tooth correction means are used in order to achieve a desired arrangement of the teeth with respect to each other. The tooth correction means 1 comprises several tooth top parts which, as an example, are attached at tooth surfaces 3 of all teeth and which are coupled to each other by a connecting means 4 for instance having a wire shape. The connecting means 4 enables the transmission of forces and, if required, also torques between the teeth in order to bring the teeth in a predeterminable position during orthodontic therapy. In the prior art tooth correction means, the tooth top parts clearly extend further from the teeth and the wire thickness of the connecting means is clearly selected to be thicker.

Figure 2:
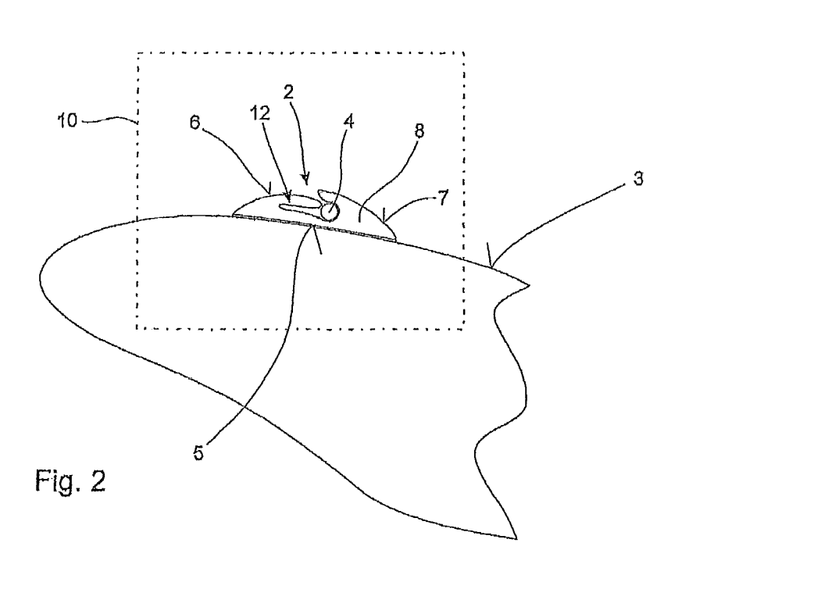
FIG. 2 is a lateral view of a first embodiment of a tooth top part in a functional position.

As can be seen from FIG. 2, the tooth top part 2 according to the invention, which is identical to the base body in the present embodiment, comprises a tooth support surface 5 by means of which it is bonded to the tooth surface 3 in a known manner. The tooth support surface 5 is flanked by a first outer surface 6 and a second outer surface 7 each of which includes an acute angle 18, 19 (FIG. 4) with the tooth support surface 5. Transitional regions between the outer surfaces 6, 7 and the tooth support surface 5 are formed with a rounding-off radii 20, 21.

In the shown embodiment of the tooth top part 2, end faces 8, 9 of the tooth top part 2 are orthogonal to the outer surfaces 6, 7 and to the tooth support surface 5. Thus, the end faces 8, 9 in the shown embodiment of the tooth top part 2 are parallel to a cross-sectional plane identical to the drawing plane of FIGS. 2 and 4.

Figure 4:
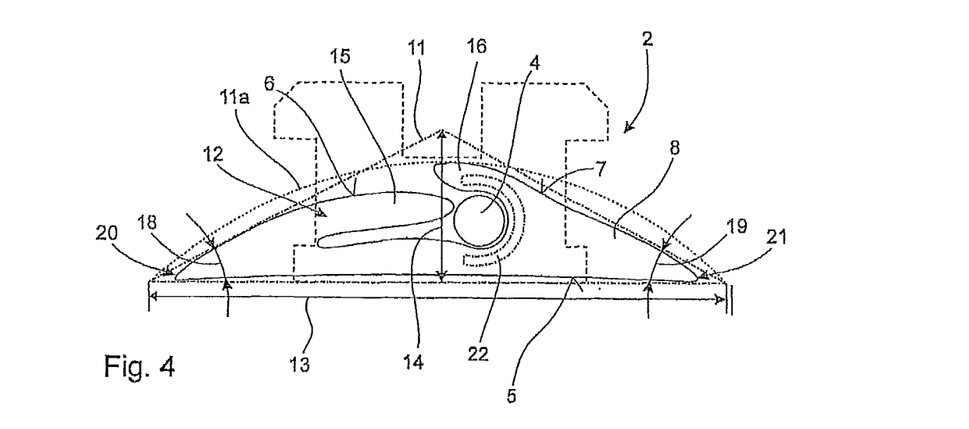
FIG. 4 is a schematic view of the tooth top part according to FIGS. 2 and 3.

As can be seen from the schematic view of FIG. 4, a cross section of the tooth top part 2 is formed such that it is contained within a triangular envelope 11 or within a circular section shaped envelope 11a. A mean perpendicular 14 of the envelope 11 is orthogonal to a base line 13 of the envelope 11, determined by the tooth support surface 5. A length of the mean perpendicular 14 is less than 50 percent, in the present example about 40 percent, of the length of the base line 13, which results in a low profile for the tooth top part 2, thus causing less irritations of the mouth mucous membrane (not shown).

Figure 3:
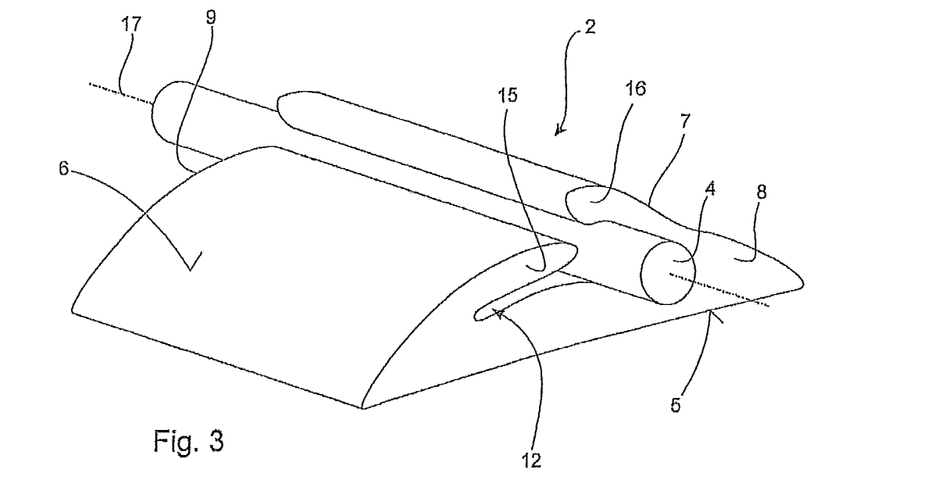
FIG. 3 is a perspective view of the tooth top part according to FIG. 2.

In the embodiment of a tooth top part shown in FIGS. 2 through 4, a recess 12 extending normally to the cross sectional plane 10 is provided with a substantially L-shape profile. For instance, the tooth top part 2 is formed as a geometrically extruded component having a constant cross section normal to the cross sectional plane Ia throughout its length. Thus, the recess 12 also extends with a constant cross section and thus, determines a guiding axis 17 coinciding with a central axis of the for instance wire-shaped connecting means 4 having a circular cross section.

Due to the substantially L-shaped profile design, a snap-on nose 15 and a snap-on hook 16 for immobilizing/securing the connecting means are formed in the base body 2 of the tooth top part. The snap-on nose 15 is designed for locking the connecting means 4 in the shown functional position within the snap-on hook 16, thus guaranteeing a safe, positive locking (form locking) immobilization of the connecting means 4 at the tooth top part 2 crosswise/transverse to the extension of the connecting means 4. During an assembly operation (not shown), where the connecting means 4 is pushed transversely to its longitudinal extension into the recess 12, both the snap-on nose 15 and the snap-on hook 16 undergo elastic deformation. During the assembly operation, while the snap-on nose 15 is bent toward the tooth support surface 5, the snap-on hook 16 undergoes deformation in the opposite direction. As a result, the recess 12 opens up a cross section enabling insertion of the connecting means 4. As a result of a preferably exclusively elastic deformation of the snap-on nose 15 and the snap-on hook 16, the tooth top part is self-locking for the connecting means 4.

As soon as the connecting means 4 arrives at the functional position shown in FIGS. 2 through 4, the resilience, i.e. elastic restoration forces, of the snap-on nose 15 and the snap-on hook 16 will have a non-positive locking (force locking) and positive locking (form locking) effect for forces occurring within the cross sectional plane Ia without requiring any additional measures to that end. Both the snap-on nose 15 and the snap-on hook 16 comprise elastic regions formed as solid-state joints enabling elastic pivoting into the assembly position and restoration into the functional position.

In a variant of the tooth top part 2, the snap-on hook 16 may be reinforced using an insert 22, preferably made of an elastic/resilient metal, as shown in FIG. 4.

In the following description of a second embodiment of a tooth top part 22 shown in FIG. 5, components with identical function are given reference numerals increased by 20. The tooth top part 22 is provided for receiving a connecting means 24 having a rectangular cross section in the present case and which enables the transmission of torque between neighbouring tooth top parts 22. The recess 32 is adapted to the connecting means 24 such that the latter engages the snap-on hook 36 via three lateral surfaces and is pressed by the snap-on nose 35 into this region of the recess 32.

Figure 5:
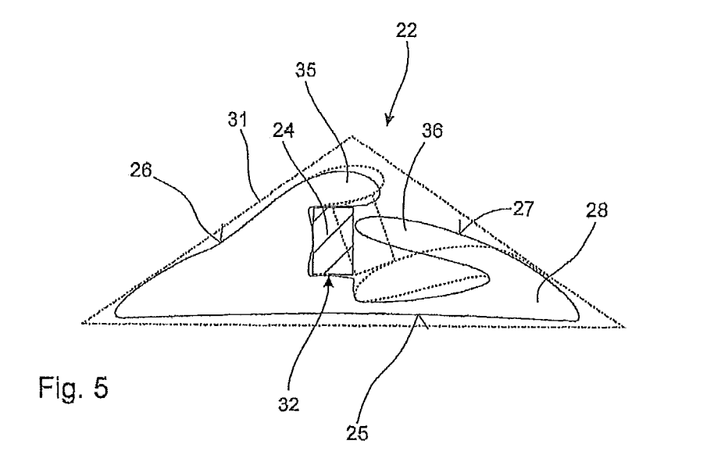
FIG. 5 is a lateral view of a second embodiment of a tooth top part in a functional position shown as solid lines and in an assembly position shown as dotted lines.

As can be seen from the dotted-line representation of FIG. 5, when the connecting means 24 is mounted, the snap-on nose 35 is 10 supposed to be bent downward while the snap-on hook is deformed downward toward the tooth support surface 25. This causes the recess 32 to open up a cross section through which the connecting means 24 can be brought into the functional position, as it exists in the solid-line representation of FIG. 5. After the connecting means 24 has reached the functional position, the snap-on nose 35 and the snap-on hook 36 will pivot back elastically into the initial position shown with solid lines and thus, will cause positive locking (form locking) of the connecting means.

Demounting of the connecting means 24 can be effected by holding down the snap-on nose 35 toward the tooth support surface 25 with a tool (not shown) and subsequently pivoting the connecting means 24 out of the recess 32 by performing a pivoting movement while deforming the snap-on hook 36.

Figure 6:
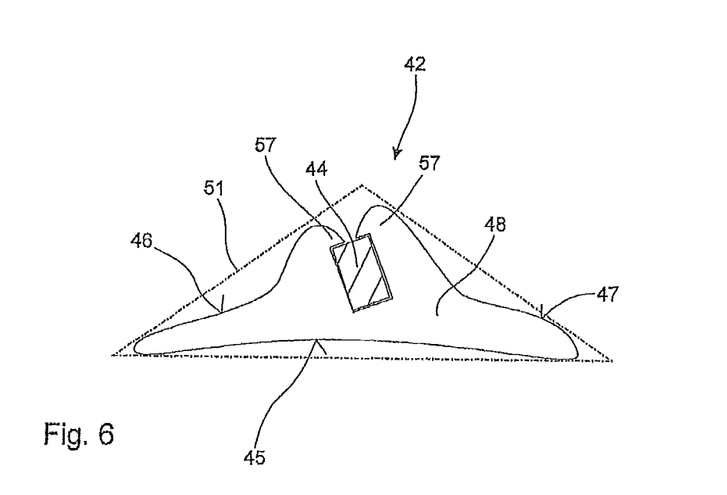
FIG. 6 is a lateral view of a third embodiment of a tooth top part in a functional position.
Figure 7:
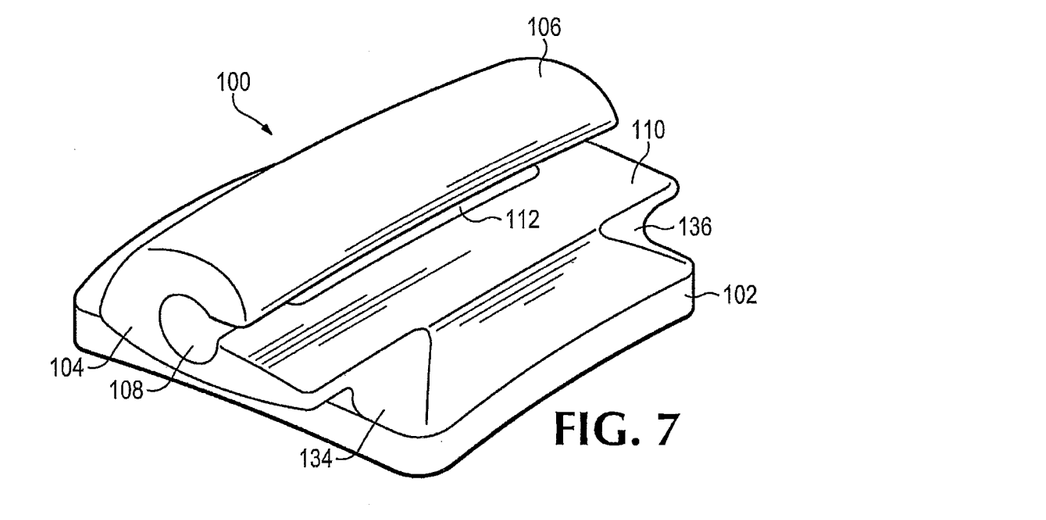
FIG. 7 is a perspective view of another embodiment of a low profile bracket.

A simplified embodiment of a tooth top part 42 is shown in FIG. 6. In this case, the cross section of the recess 52 substantially corresponds to the cross section of the connecting means 44 and is only limited by barbed hooks 57 provided on both sides in the region of the groove opening. These barbed hooks 57 are elastically displaced when the connecting means 44 is inserted into the recess 52, and will move back into the shown position as soon as the connecting means 44 has reached the functional position. The advantage of the embodiment according to FIG. 6 can be considered as having no hollow spaces at the tooth top part 42 due to the corresponding cross sections of the connecting means 44 and the recess 52. Demounting of the connecting means 44 is preferably effected by pulling it out laterally toward the guiding axis oriented normally to the drawing plane of FIG. 6.

The tooth top parts 2, 22, 42 shown in FIGS. 2 through 6 are preferably made of a synthetic material such as a plastics material. Alternatively, the use of ceramics or metal for producing the tooth top parts is possible. In doing so, it may be necessary to modify the geometries of the tooth top parts, in particular in the region of the solid-state joints, in order to guarantee the desired elastic properties. When using synthetic materials such as plastic materials or ceramic materials for the tooth top parts, a regional/sectional reinforcement employing metal inserts may be provided.

The tooth top part 2, 22, 42 according to the invention enables relative displacement and/or pivoting of neighbouring teeth. Given that the tooth top part 2, 22, 42 does not have any hooks and eyelets (no "nooks and crannies"), no additional connecting elements such as rubber bands can be inserted. In order to provide for additional force application to the teeth to be corrected, additional hooks may be provided in the region of the gum line. These additional hooks, which may be attached in a structurally separated manner from the tooth top parts 2, 22, 42 at selected or all teeth and which are preferably made of synthetic material, enable additional connecting elements to be hooked up which are typically significantly shorter than the tooth top parts 2, 22, 42 and, as they are suited exclusively for hooking up additional connecting elements, can be designed in a very skinny fashion. By providing additional hooks in the region of the gum line, these hooks as well can be placed very inconspicuously and in particular at particularly suitable force application points on the teeth to be moved, since this will favor parallel displacement of the teeth. Due to the decoupling of the different force application systems, which are determined by the tooth top parts 2, 22, 42 on one hand and by the additional hooks on the other hand, not only an optically inconspicuous attachment of the corresponding components for the tooth correction means with little irritation of the mouth mucous membrane, but also a particularly efficient movement of the teeth due to the advantageous selectability of the force application points can be achieved.

In another aspect of the invention, a bracket 100 as shown in FIGS. 7-11 includes a base 102 and a top portion 104. The brackets 100 are affixed to teeth 101 (shown in dashed outline). The base 102 has a width in both the gingival-occlusal plane ($L_1$) and a length in the distal-anterior direction ($W_1$). The top portion 104 is made of an elastically deformable hook portion 106 that curls around past the apex to create a substantially cylindrical or tubular archwire channel 108. Note that the interior of this channel could also be rectangular in cross section as shown in the embodiment of FIG. 6. In this embodiment, the snap-on nose is eliminated and a shelf 110 is formed underneath the hook portion 106. The shelf and the distal end of the hook portion 106 form an opening 112 that is slightly smaller than the largest diameter of an archwire 114 (dashed outline in FIG. 9). When the archwire 114 is press fitted into the opening 112, the hook portion 106 elastically deforms allowing the archwire to enter the channel 112. Once the archwire 114 has reached its functional position, the hook snaps back, securing the archwire 114 therein. The archwire may be removed by prying the hook portion 106 upward with a tool (not shown).

Figure 12:
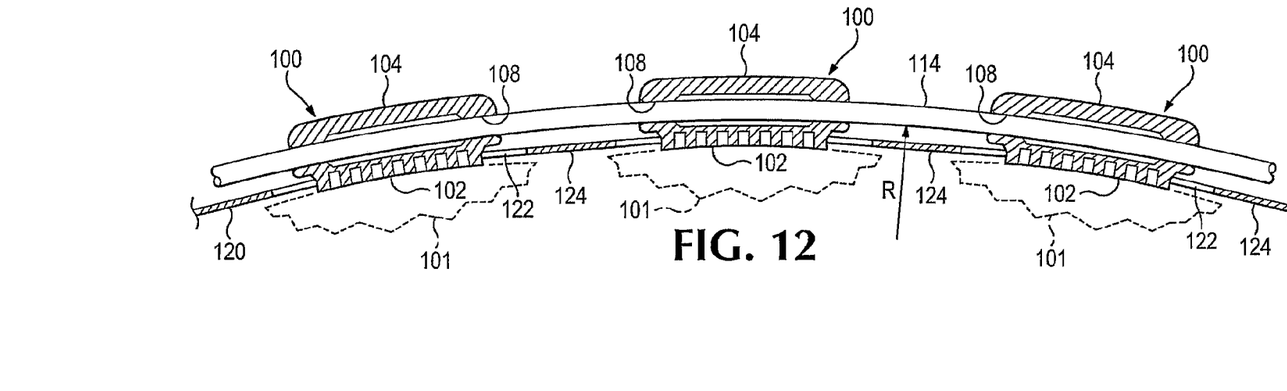
FIG. 12 is a side cutaway view of the brackets of FIG. 11.

The archwire 114 for this bracket is thin. Treatment typically begins with an archwire having a diameter of 0.010". It progresses during the treatment to 0.012" and eventually to 0.014". All archwires fit within the bracket 100, which has a nominal channel diameter of 0.016". As shown in FIG. 12, the archwire channel is larger in the center portion of the bracket for reducing friction.

The archwire has a radius of curvature "R" as also shown in FIG. 12. The interior shape of the hook portion (and hence, of the archwire channel 108) of the top part in the distal-anterior direction is curved and has a radius of curvature made to match the radius of curvature "R" of the archwire. This insures that the archwire slides through the channel with the least amount of friction possible.

Figure 11:
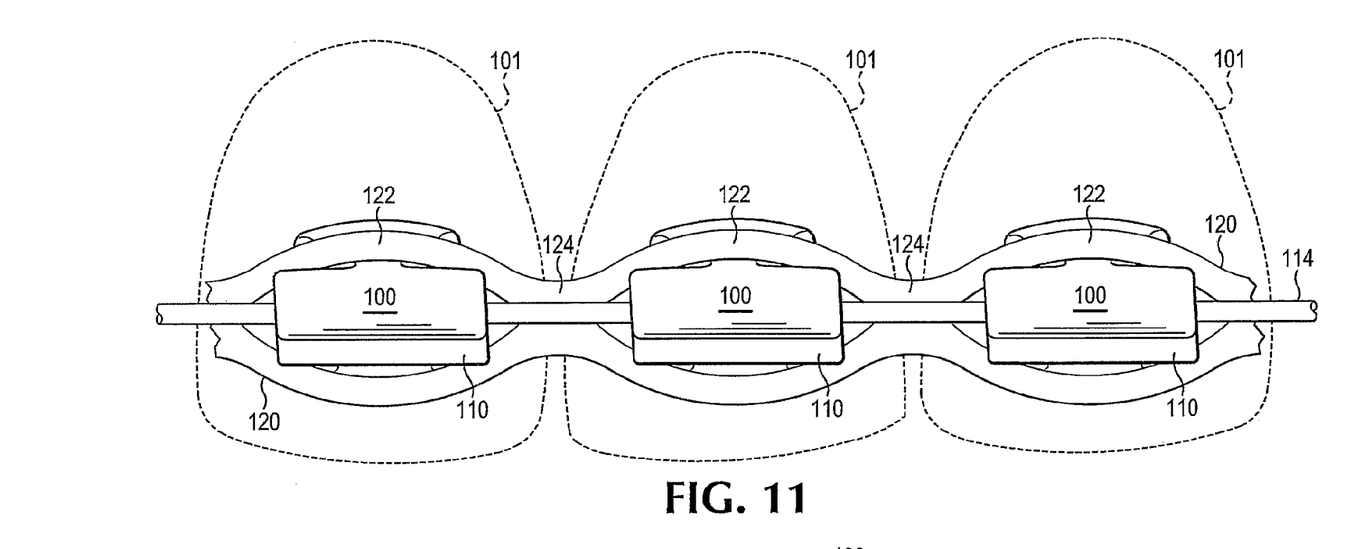
FIG. 11 is a top view of the brackets of FIG. 8 installed on a patient's teeth in dashed outline and connected by a power chain.

The base and the top portion may be configured to provide a tie wing for an elastic power chain 120. An elastic power chain (see FIG. 1) is an elastic band with at least two open loops 122 joined by bridge portions 124. The power chain 120 has three loops and can be looped about adjacent brackets so as to exert a compressive force tending to draw them together as shown in FIG. 11. The power chain may have any number of loops desired.

Figure 8:
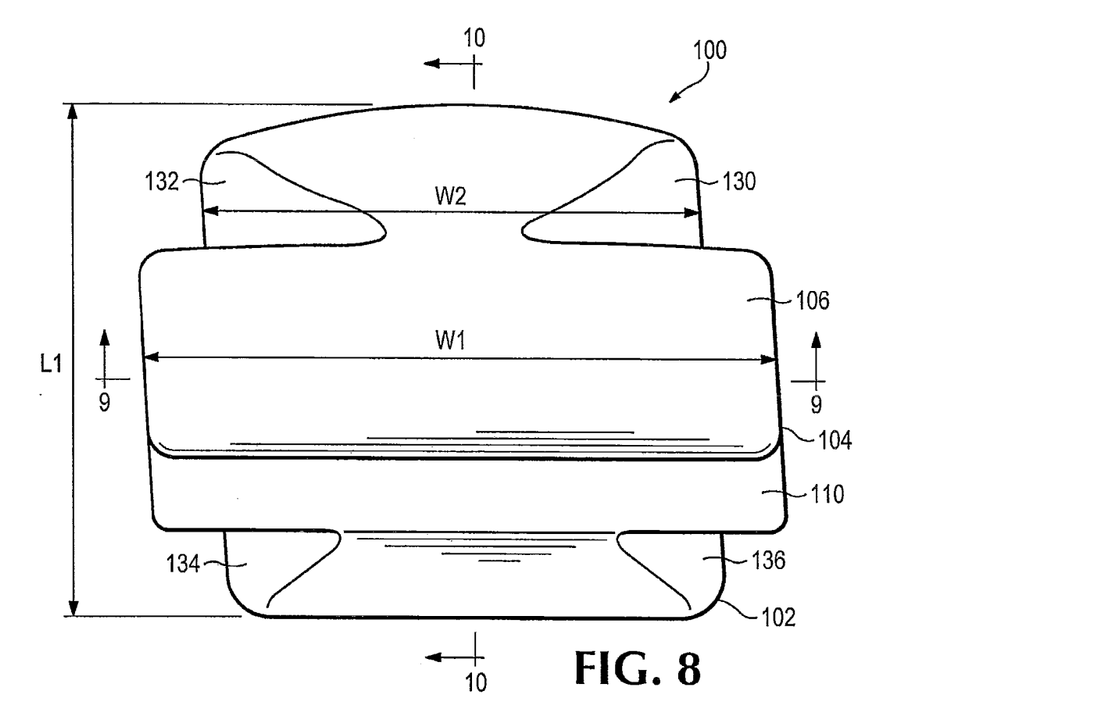
FIG. 8 is a top view of the bracket of FIG. 7.
Figure 9:
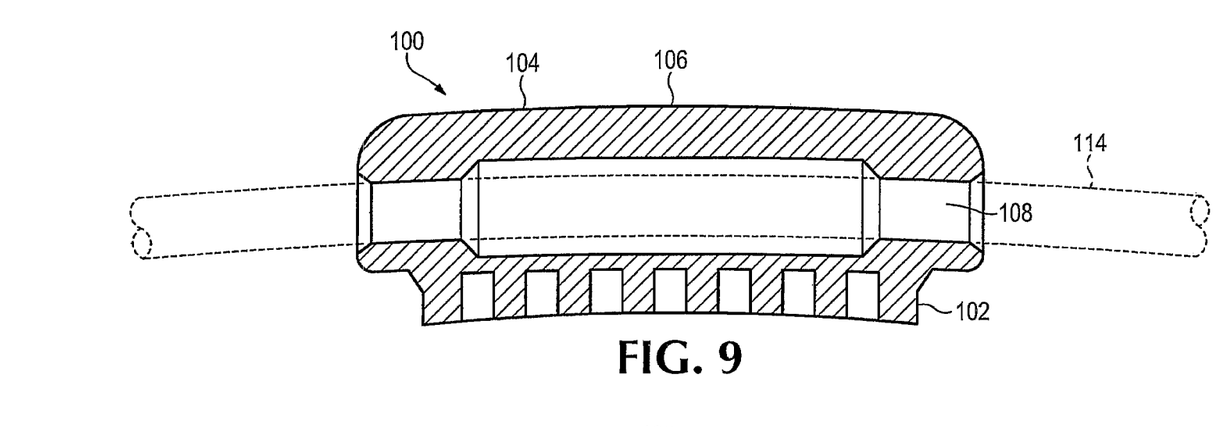
FIG. 9 is a cutaway side view taken along line 9-9 of FIG. 9 with an archwire shown in dashed outline.
Figure 10:
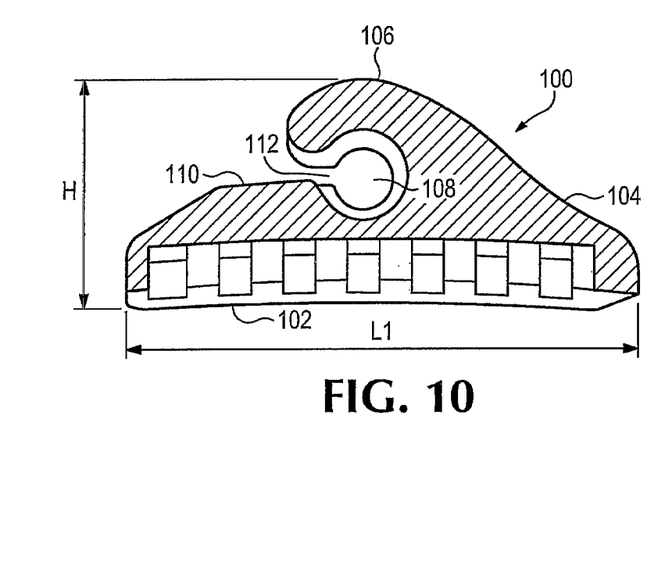
FIG. 10 is a cutaway view taken along line 10-10 of FIG. 8.

To form a tie wing, the top portion 104 is made longer in the distal-anterior direction than the width of the base 102 in this same direction as shown in FIG. 8 by the arrows designating W1 and W2. In addition, the base 102 may be chamfered at its corners so that the power chain 120 is retained more easily when it is looped over the top of the bracket. The corners 130, 132, 134 and 136 are all chamfered to provide a surface for retaining the power chain loops 122.

The bracket 100 is a small low-profile bracket in which the mean height "h" is less than half of the length $L_1$ of the base 102 in the gingival-occlusal direction. The low profile insures that the bracket will not irritate the inside of the lips of the patient. Typical dimensions are that the gingival-occlusal length of the base is about 0.135". Thus, the bracket could be 0.140" to 0.130" inches in length. The low profile comes from the height of the bracket, which in a preferred embodiment is about 0.053", but could range, preferably, from about 0.048" to 0.058". The height of the bracket, however, should not exceed half of the gingival-occlusal length. Thus if the length were 0.130", the bracket height should not exceed 0.065". This results in a bracket that is triangular in cross section with a rounded crown at the apex. The triangle is a shallow low-profile shape that makes the bracket comfortable for the patient and is easy to adjust.

The terms and expressions that have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. An orthodontic bracket comprising a base adapted to be affixed to a tooth, the base having a maximum width extending in the gingival-occlusal direction, a top portion having an archwire channel defined by an elastically deformable hook member which extends from the base to a maximum height no greater than half of said maximum width, the top portion further including a shelf providing an opening to said archwire channel beneath said hook member such that said hook member elastically deforms when an archwire is pressed into said opening and snaps closed when the archwire reaches a functional position, wherein said top portion has a length which exceeds a width of the base in the distal-anterior direction so as to form a tie wing.

2. The orthodontic bracket of claim 1 wherein said base includes chamfered surfaces for supporting an elastic power chain, said power chain comprising a pair of elastically resilient loops joined by a central bridge.

3. The orthodontic bracket of claim 1 wherein said deformable hook member overlies said shelf in the labial direction.

4. The orthodontic bracket of claim 1 wherein said archwire channel is tubular.

5. The orthodontic bracket of claim 1 wherein the maximum height of said hook member does not exceed 0.53 inches.

* * * * *